United States Patent [19]

Snyder

[11] Patent Number: 5,721,463

[45] Date of Patent: Feb. 24, 1998

[54] METHOD AND APPARATUS FOR TRANSFERRING HEAT FROM TRANSDUCER ARRAY OF ULTRASONIC PROBE

[75] Inventor: Jonathan E. Snyder, Whitefish Bay, Wis.

[73] Assignee: General Electric Company, Milwaukee, Wis.

[21] Appl. No.: 580,564

[22] Filed: Dec. 29, 1995

[51] Int. Cl.$^6$ .................................................. H01L 41/08
[52] U.S. Cl. .......................... 310/334; 310/327; 310/341
[58] Field of Search ........................... 310/327, 334–336, 310/340–342, 344

[56] References Cited

U.S. PATENT DOCUMENTS

| | | | |
|---|---|---|---|
| 2,789,557 | 4/1957 | Davis, Jr. | 310/341 X |
| 3,424,930 | 1/1969 | List et al. | 310/341 X |
| 3,518,766 | 7/1970 | Burt | 310/341 X |
| 5,225,734 | 7/1993 | Nakanishi | 310/341 X |
| 5,427,106 | 6/1995 | Breimesser et al. | 128/661.01 |
| 5,541,468 | 7/1996 | Frey et al. | 310/334 |
| 5,545,942 | 8/1996 | Jaster et al. | 310/341 |
| 5,584,183 | 12/1996 | Wright et al. | 62/3.7 |
| 5,598,051 | 1/1997 | Frey | 310/334 |

*Primary Examiner*—Mark O. Budd
*Attorney, Agent, or Firm*—Dennis M. Flaherty; John H. Pilarski

[57] ABSTRACT

A device for improving thermal transfer inside an ultrasound probe and reducing heat build-up near the transducer face. The cable components are used as heat conductors which conduct heat out of the probe handle. These heat pipes are coupled to an internal heat conductor which is in heat conductive relationship with the transducer pallet. Thus, heat generated by the transducer array can be transferred, via the internal heat conductor plate and the cable heat conductors, away from the probe surface which contacts the patient. A heat conductive structure can be embedded in the overall shield braid of the cable. Suitable heat conductive structures include thread or wire made of material having a high coefficient of thermal conductivity, as well as narrow tubing filled with heat conductive fluid. Alternatively, inlet and return flow paths for cooling fluid are incorporated in the cable. The inlet and return flow paths inside the cable are respectively connected to the inlet and outlet of a flow path which is in heat conductive relationship with an internal heat conductor in the probe handle.

11 Claims, 7 Drawing Sheets

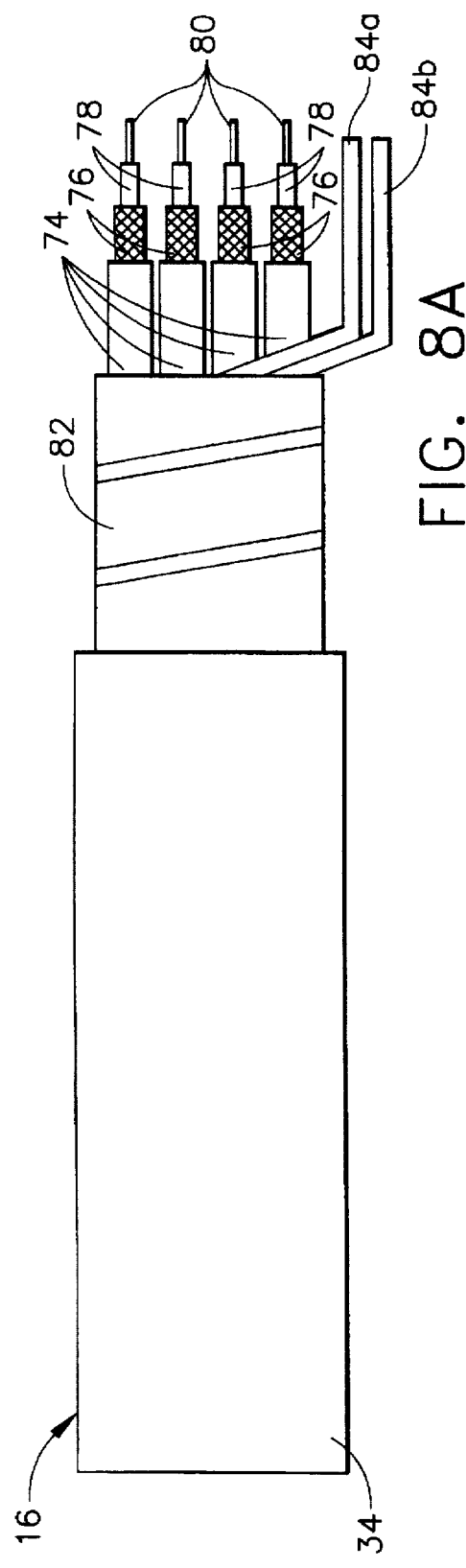
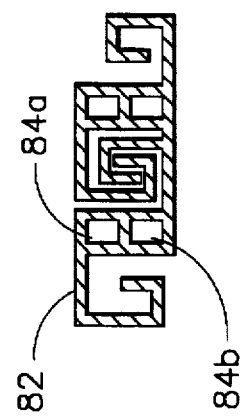
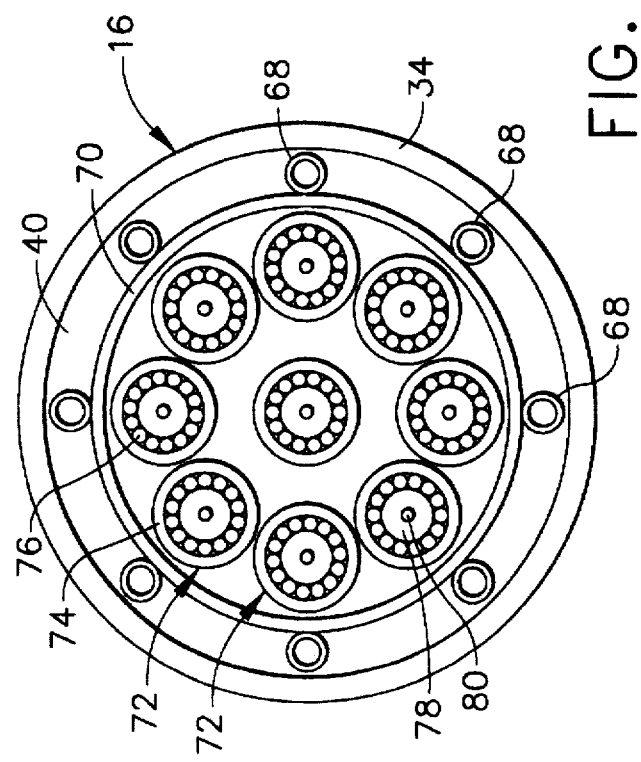
FIG. 8A
FIG. 8B
FIG. 7

METHOD AND APPARATUS FOR TRANSFERRING HEAT FROM TRANSDUCER ARRAY OF ULTRASONIC PROBE

FIELD OF THE INVENTION

This invention generally relates to probes used in ultrasonic imaging of the human anatomy. In particular, the invention relates to techniques for limiting the build-up of transducer-generated heat on the exterior of an ultrasound probe.

BACKGROUND OF THE INVENTION

A conventional ultrasonic probe comprises a transducer pallet which must be supported within the probe housing. As shown in FIG. 1, a conventional transducer pallet 2 comprises a linear array 4 of narrow transducer elements. Each transducer element is made of piezoelectric material. The piezoelectric material is typically lead zirconate titanate (PZT), polyvinylidene difluoride, or PZT ceramic/polymer composite.

Typically, each transducer element has a metallic coating on opposing front and back faces to serve as electrodes. The metallic coating on the front face serves as the ground electrode. The ground electrodes of the transducer elements are all connected to a common ground. The metallic coating on the back face serves as the signal electrode. The signal electrodes of the transducer elements are connected to respective electrical conductors formed on a flexible printed circuit board (PCB) 6.

During operation, the signal and ground electrodes of the piezoelectric transducer elements are connected to an electrical source having an impedance $Z_S$. When a voltage waveform is developed across the electrodes, the material of the piezoelectric element compresses at a frequency corresponding to that of the applied voltage, thereby emitting an ultrasonic wave into the media to which the piezoelectric element is coupled. Conversely, when an ultrasonic wave impinges on the material of the piezoelectric element, the latter produces a corresponding voltage across its terminals and the associated electrical load component of the electrical source.

The transducer pallet 2 also comprises a mass of suitable acoustical damping material having high acoustic losses positioned at the back surface of the transducer element array 4. Backing layer 12 is acoustically coupled to the rear surface of the transducer elements, via the acoustically transparent PCB 6, to absorb ultrasonic waves that emerge from the back side of each element so that those waves will not be partially reflected and interfere with the ultrasonic waves propagating in the forward direction.

Typically, the front surface of each transducer element of array 4 is covered with at least one acoustic impedance matching layer 8. The impedance matching layer 8 transforms the high acoustic impedance of the transducer elements to the low acoustic impedance of the human body and water, thereby improving the coupling with the medium in which the emitted ultrasonic waves will propagate.

The transducer element array, backing layer and acoustic impedance matching layer are all bonded together in a stack-up arrangement, as seen in FIG. 1. During assembly of the ultrasonic probe, the transducer stack-up must be held securely within the probe housing. Typically, this is accomplished by securing the transducer stack-up within a four-sided array case (not shown), i.e., a "box" having four side walls but no top or bottom walls. The array case is made of electrically conductive material and provides a common ground for connection with the ground electrodes of the transducer elements. The transducer stack-up is inserted into a recess in the array case until the bottom surface of the acoustic impedance matching layer 8 is flush with the bottom edge of the array case. The transducer stack-up is conventionally bonded inside the array case using epoxy. Then a second acoustic impedance matching layer is conventionally bonded to those flush bottom surfaces.

In conventional applications, each transducer element produces a burst of ultrasonic energy when energized by a pulsed waveform produced by a transmitter (not shown). The pulses are transmitted to the transducer elements via the flexible PCB 6. This ultrasonic energy is transmitted by the probe into the tissue of the object under study. The ultrasonic energy reflected back to transducer element array 4 from the object under study is converted to an electrical signal by each receiving transducer element and applied separately to a receiver (not shown).

The release of acoustic energy during transmission creates a thermal build-up in the probe due to acoustic losses being converted into heat. The amount of heat that can be allowed to build up on the exterior of an ultrasound probe must be within prescribed limits. Typically the limit is that the temperature on the patient contact surface of the probe cannot exceed 41° C. or 16° C. above ambient temperature, whichever is smaller. Most of the heat tends to build up immediately around the transducer elements, which are necessarily situated in the probe very close to the body of the patient being examined.

During assembly of an ultrasonic probe incorporating the structure of FIG. 1, transducer pallet 2 must be secured within the probe housing. The interior volume of the probe housing surrounding the transducer pallet is filled with thermally conductive potting material, e.g., heat-conductive ceramic granules embedded in epoxy. The potting material stabilizes the construction and assists in dissipating heat, generated during pulsation of the transducer element array, away from the probe surface/transducer face toward the interior/rear of the probe.

Conventional thermal management in ultrasound probes is accomplished with relatively simple devices such as heat conductors, which are buried in the transducer structure so that they transfer heat from the source into the body of the probe structure as quickly as possible. In this way heat is conducted, from the critical front surface of the probe into the handle where the increased mass helps dissipate the heat evenly.

For example, U.S. patent application Ser. No. 08/343,063 discloses the employment of foil heat conductors made of heat conductive, electrically nonconductive material. The foil heat conductors are placed around the periphery of the transducer pallet (but within the probe housing) so that heat can be drawn away from the transducer face and toward the rear/interior of the probe. These heat conductors act as conduits for draining heat from the thermal potting material which fills the spaces inside the probe housing. Thus, the heat conductors are effectively thermally coupled to the transducer element array. This arrangement increases the ability to dissipate heat away from the transducer pallet and thus away from the patient being examined. U.S. patent application Ser. No. 08/343,063 also discloses that the internal heat conductors can be thermally coupled to the shielding braid of the coaxial cable. Connection to the shielding braid facilitates the wicking away of even more heat from the transducer element array. By soldering the overall shield into a metal foil structure which is in contact with the internal heat conductors, heat generated by the pallet can be conducted into the cable and dissipated throughout the 2-m length of the cable. Internal potting with thermally conductive epoxy also helps provide additional contact to the shield and the individual shields of the individual signal wires inside the cable.

Ultrasonic transducer technology is rapidly evolving towards probes with higher element counts. This in turn requires more cabling and lighter-weight materials, and challenges the manufacturability of the interconnect between the individual elements and the ultrasonic imaging system. Added to this strain on the packaging technology is the availability of high levels of circuit integration in semiconductors. Because of the electrical impedance mismatch between the small elements in the transducer and the sensing electronics in the system, a number of investigators have developed means to provide active electronics within the transducer handle. As electronic technology advances, it is expected that more active circuitry will be placed as near to the source of the detected signal as possible.

The application of semiconductor technology to the diagnostic ultrasonic transducer has created a new dimension in the design and fabrication of these devices. Whereas these products have traditionally been composed of passive electronic circuits and sensors of piezo-electric ceramic, the transducer is now host to active preamplifiers, transmitters, lasers, and ultimately, A/D converters and perhaps digital signal processing. The addition of this technology into the traditionally "hand-held" ultrasonic probe creates severe strains on the ability of the mechanical designer to dispose of the heat generated by the active devices, thereby exacerbating the difficulty of thermal management within the transducer. In order to make the highest quality images, the power output of the probe is managed close to the regulatory limit, creating a need to manage the thermal output of the probe.

Thus, with the advent of active devices, the above-described use of heat conductors will no longer be sufficient to handle the heat load within the transducer. For example, the heat load dissipated by the simple devices available today is approximately 1 W. If preamplifiers are introduced into the system which dissipate 10 mW in a quiescent mode, the heat load will be increased by 2 W for a 200-element probe. Because the current designs are sometimes limited by the temperature of the patient contact area, there is little margin to accommodate this type of thermal output increase. Thus, there is a need to provide thermal transfer mechanisms capable of dissipating greater amounts of heat.

SUMMARY OF THE INVENTION

The present invention is a device for improving thermal transfer inside an ultrasound probe and reducing heat build-up near the transducer face. The invention is based on the concept of using the coaxial cable as a tool in managing the thermal problem created by the incorporation of active electronics in the handle of an ultrasonic probe. In accordance with preferred embodiments of the invention, the cable components are used as heat conductors which conduct heat out of the probe handle. These heat pipes are coupled to an internal heat conductor, made of a sheet or plate of heat conductive material, which is embedded in the backing layer material of a transducer pallet. Thus, heat generated by the transducer array can be transferred, via the internal heat conductor and the cable heat conductors, away from the probe surface which contacts the patient.

The cable assembly in an ultrasonic probe is composed of multiple coaxial cables bundled together and covered with an overall braided shield. Each individual coaxial cable comprises a plurality of individual conductors surrounded by a twisted shield. In accordance with the thermal management design of the invention, these heat conductive structures can serve as thermal transfer devices when thermally coupled to an internal heat conductor of the probe handle. Alternatively, a heat conductive structure can be embedded in the overall shield braid of the cable. Suitable heat conductive structures include thread or wire made of material having a high coefficient of thermal conductivity, as well as narrow tubing filled with heat conductive fluid.

In accordance with a further aspect of the present invention, inlet and return flow paths for cooling fluid are incorporated in the cable. The inlet and return flow paths inside the cable are respectively connected to the inlet and outlet of a flow path which is in heat conductive relationship with an internal heat conductor in the probe handle. In the case of forced recirculation, the cooling fluid is pumped from the cable return flow path to the cable inlet flow path. Alternatively, recirculation can be induced by cooling a portion of the cable flow path formed by connecting the cable return flow path directly to the cable input flow path, thereby generating a thermal gradient which draws heat out of the probe handle.

Thus, the invention solves the problem of how to transfer heat out of the probe handle in a manner so that the temperature of the probe part which contacts the patient does not exceed a predetermined upper limit. In particular, the invention provides a mechanism for dissipating heat generated inside the probe handle in a manner that leaves the patient unaware of the heating effect.

BRIEF DESCRIPTION OF THE DRAWINGS

FIG. 7 is a schematic sectional view showing the cable of an ultrasonic probe in accordance with a fourth preferred embodiment of the invention wherein heat conductors are embedded in a cable shield.

FIG. 8A is a schematic diagram showing the armored cable of an ultrasonic probe in accordance with a fifth preferred embodiment of the invention wherein heat conductors are molded into the cable armor.

FIG. 8B is a sectional view of the armor incorporated in the probe shown in FIG. 8A.

DETAILED DESCRIPTION OF THE PREFERRED EMBODIMENTS

Figure 1:
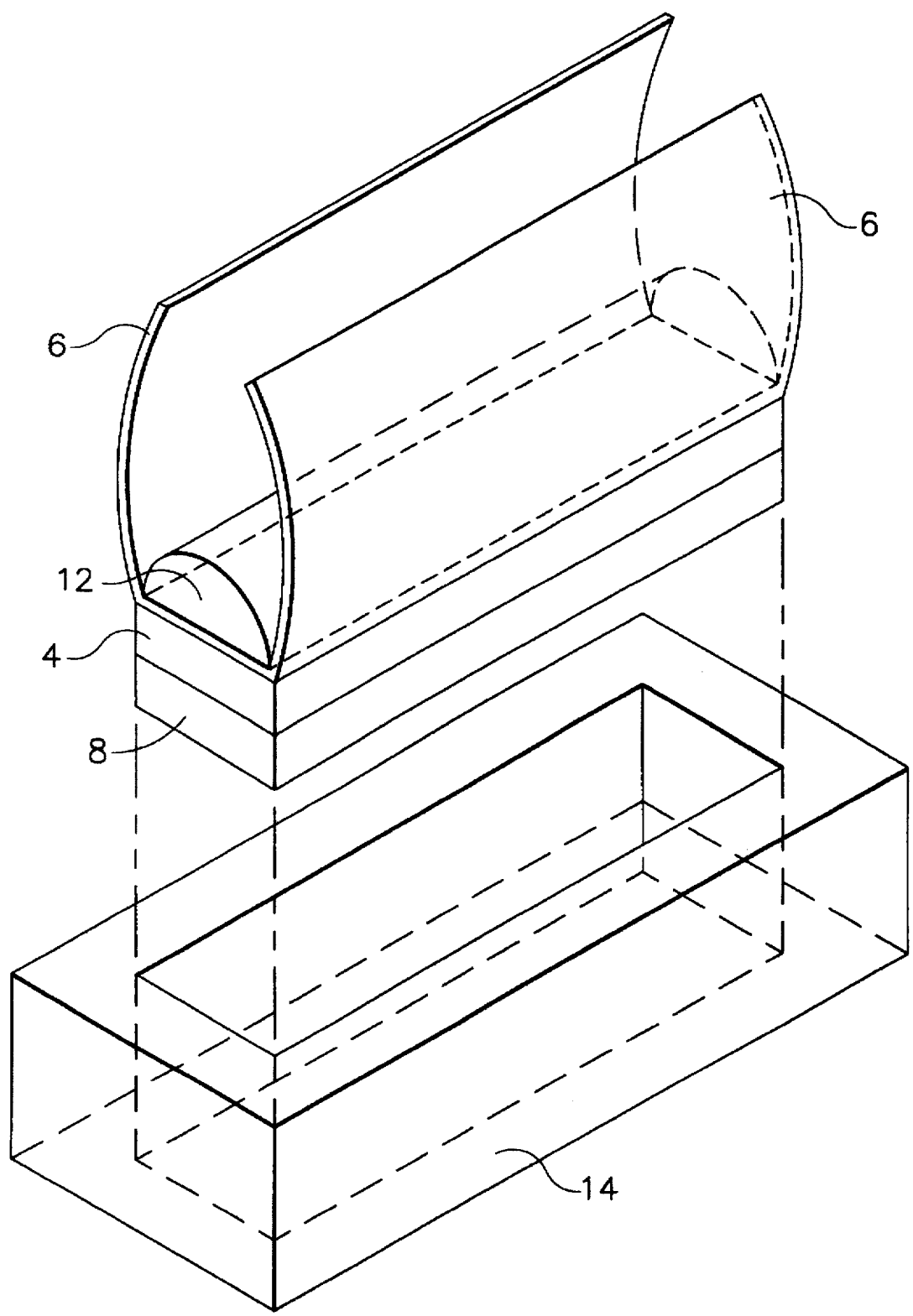
FIG. 1 is a schematic exploded view of parts of a conventional transducer pallet for use in an ultrasonic probe.
Figure 2:
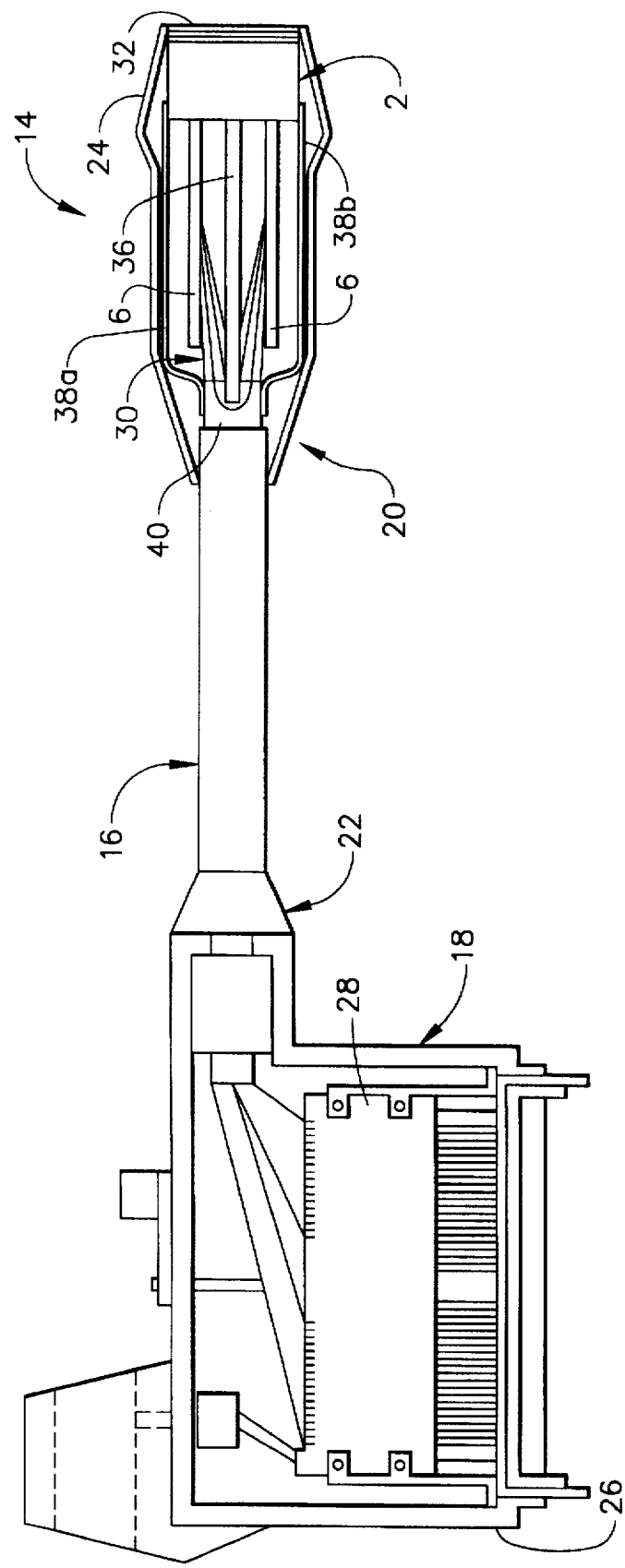
FIG. 2 is a schematic diagram showing the structure of an ultrasonic probe in accordance with a first preferred embodiment of the invention wherein the transducer pallet is thermally coupled to the cable via a soldered internal heat conductor.

Referring to FIG. 2, an ultrasound probe in accordance with the preferred embodiment of the invention comprises a probe handle 14 connected to one end of a cable 16 and a system connector 18 connected to the other end of the cable. Means 20 and 22 for relieving stress are provided at the cable/housing and system connector/cable connections, respectively. The probe handle 14 comprises a plastic shell 24 which houses a conventional transducer pallet 2. The system connector comprises a plastic housing 26 in which a PCB 28 is mounted. The signal electrodes of the transducer array are electrically connected to PCB 28 via flexible PCB 6, signal wiring 30 and a multiplicity of coaxial cables in cable 16.

Figure 3:
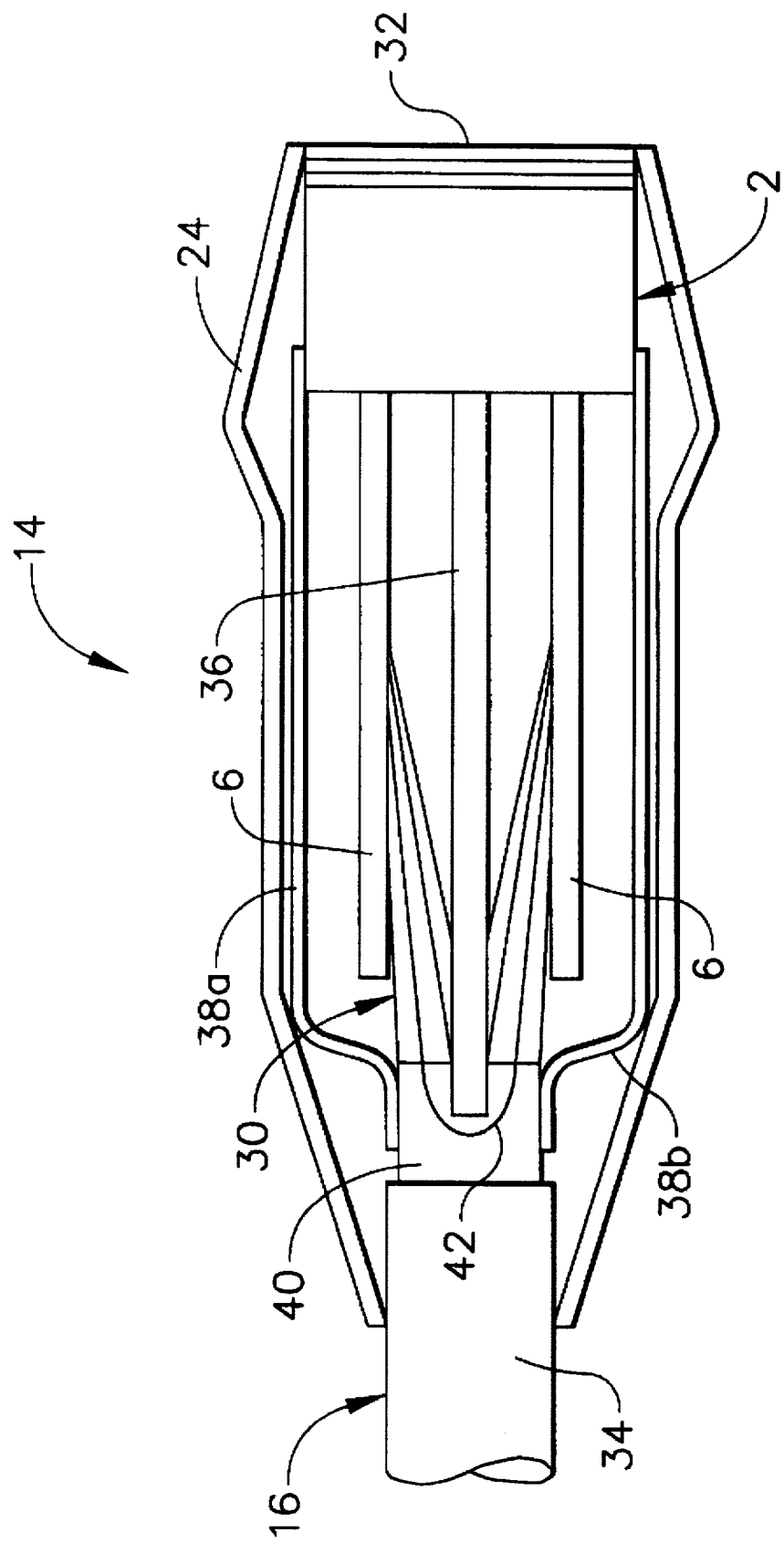
FIG. 3 is a schematic diagram showing on a magnified scale the handle of the ultrasonic probe shown in FIG. 2.

As shown on a magnified scale in FIG. 3, the probe handle 14 in accordance with a first preferred embodiment of the invention comprises a transducer pallet 2 mounted in plastic shell 24. The pallet is arranged so that the front face of the transducer array is acoustically coupled to a cylindrical focusing lens 32 which contacts the patient. The transducer pallet 2 and focusing lens 32 are mounted inside plastic shell 24 by adhesively bonding the perimeter of lens 32 in an opening of corresponding shape formed in one end of shell 24. The other end of shell 24 is attached to the cable jacket 34. In accordance with the first preferred embodiment, at least one internal heat conductor 36, made of a material having a relatively high coefficient of thermal conductivity, is thermally coupled to a central portion of the transducer pallet. In addition, external heat pipes 38a and 38b (which may also serve the function of providing electromagnetic shielding) are placed in heat conductive relationship with the lateral periphery of the pallet.

The signal electrodes of the transducer array are electrically connected to the central conductors (not shown in FIG. 3) of respective coaxial cables via conductive traces formed on flexible PCB 6 and via signal wiring 30. In this embodiment, the cable overall (braided) shield 40 is brought into the probe handle 14 through the cable strain relief and directly soldered to the heat conductor structure 36 that is connected to pallet 2. The solder bead is indicated by numeral 42 in FIG. 3. This provides the most direct and effective method of piping heat from the source into the extended heat sink formed by the cable. Likewise the external heat pipes 38a and 38b are soldered to the cable overall shield 40. The cable comprises a bundle of coaxial cables surrounded by the overall shield. In addition to (or as an alternative to) thermally coupling the internal heat conductor to the overall shield, the internal heat conductor can be thermally coupled to the shield braid of each coaxial cable in the bundle.

Figure 4A:
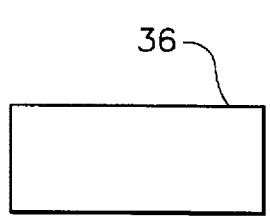
FIGS. 4A through 4F are schematic diagrams showing six variations of the internal heat conductor configuration in accordance with the preferred embodiments of the invention.
Figure 4B:
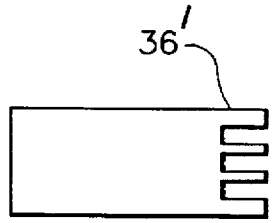
Figure 4C:
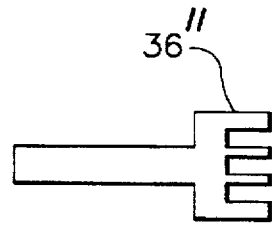

The internal heat conductor 36 may comprise a flexible sheet or stiff plate of heat conductive material having one of the configurations depicted in FIGS. 4A, 4B and 4C. The configurations depicted in FIGS. 4B and 4C comprise respective flat heat pipes 36' and 36", each having a comb-like structure which is thermally coupled to the transducer pallet by embedding the comb fingers in the backing material.

Figure 4D:
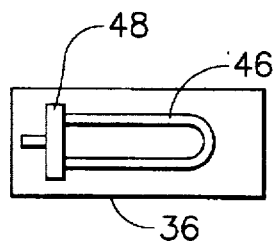
Figure 5:
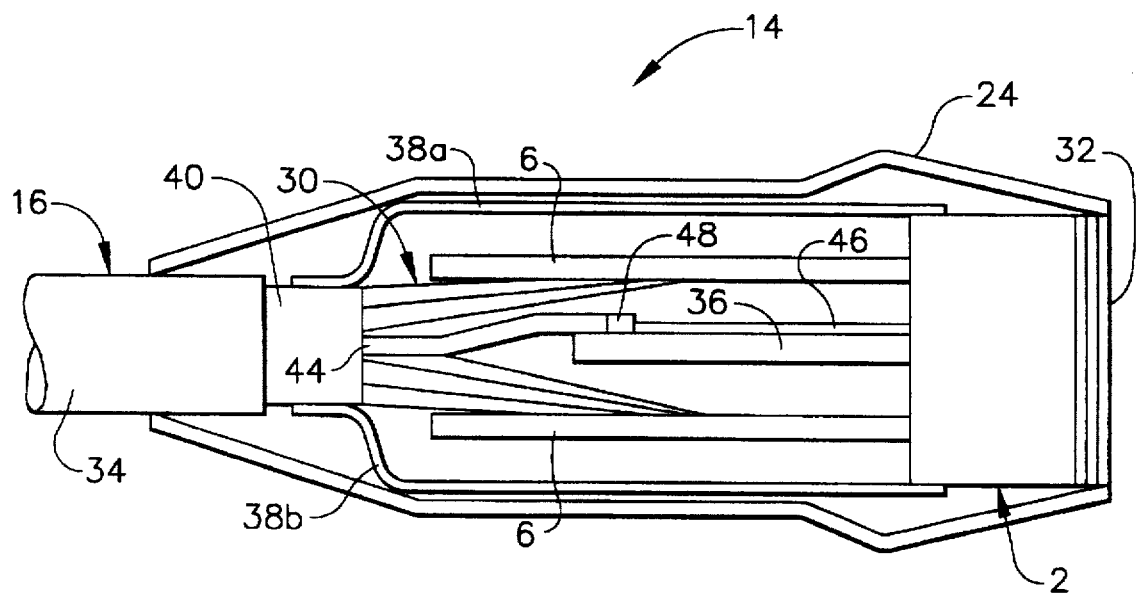
FIG. 5 is a schematic diagram showing the probe handle of an ultrasonic probe in accordance with a second preferred embodiment of the invention wherein the transducer pallet is thermally coupled to the cable via a passive fluid coupling.

In accordance with a second preferred embodiment shown in FIG. 5, the transducer pallet 2 is thermally coupled to the cable shield braid 40 via a passive fluid coupling comprising a cable fluid path 44 incorporated in the cable bundle, a fluid channel 46 mounted on and thermally coupled to the internal heat conductor 36, and a coupling joint 48 for connecting cable fluid path 44 to fluid channel 46. The fluid channel 46 may take the form of a U-shaped pipe as seen in FIG. 4D, while the cable fluid path is a pipe incorporated in the cable bundle and thermally coupled to the cable shield braid. In the latter case, the coupling joint 48 takes the form of a straight pipe in fluid communication with the ends of the legs of the U-shaped fluid channel and with an end of the cable fluid path 44, as seen in FIG. 4D. Each pipe 44, 46 and 48 may be a plastic or metal tube filled with a fluid having a relatively high thermal conductivity. Liquid metals, for example, could be used in this application provided that sufficient precautions were taken to maintain patient safety. In this embodiment, the pipes are passive, i.e., heat is transferred into the pipes passively and transferred throughout the cable without fluid motion.

Figure 4E:
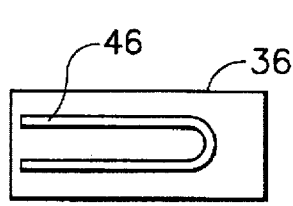
Figure 6A:
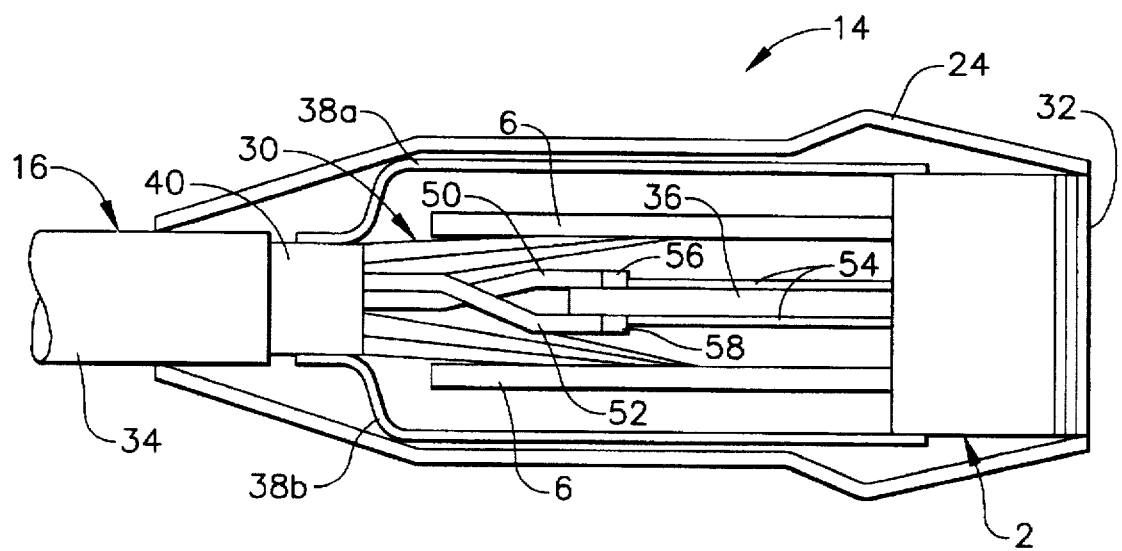
FIGS. 6A and 6B are schematic diagrams showing the probe handle and system connector, respectively, of an ultrasonic probe in accordance with a third preferred embodiment of the invention wherein the transducer pallet is thermally coupled to the cable via an active fluid coupling.
Figure 6B:
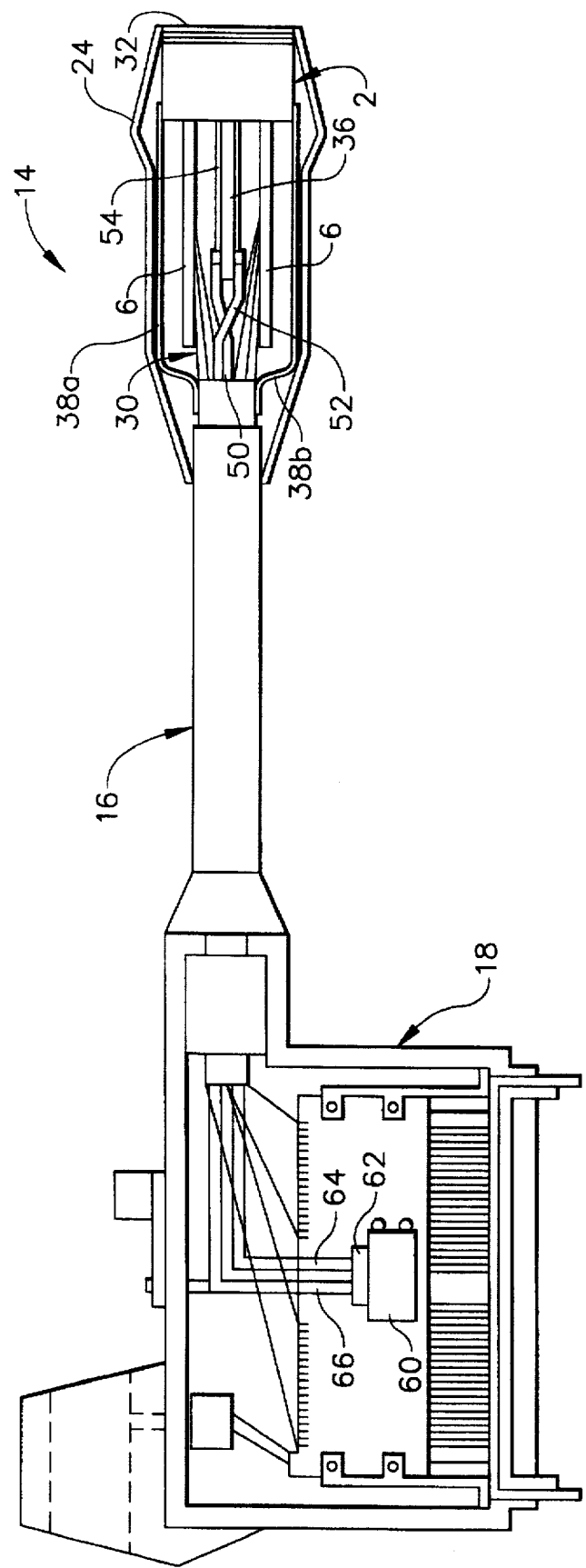

In accordance with a third preferred embodiment shown in FIGS. 6A and 6B, the transducer pallet 2 is thermally coupled to the cable shield braid 40 via an active fluid coupling comprising an input cable fluid path 50 and a return cable fluid path 52 both incorporated in the cable bundle, a fluid channel 54 mounted on and thermally coupled to the internal heat conductor 36, and coupling joints 56 and 58 for respectively connecting the input and return cable fluid paths to fluid channel 54. Like the fluid channel 46 incorporated in the embodiment of FIG. 5, the fluid channel 54 may take the form of a U-shaped pipe as seen in FIG. 4E, while the input and return cable fluid paths are respective pipes incorporated in the cable bundle and thermally coupled to the cable shield braid. One end of the input cable fluid path 50 is in fluid communication with an input leg 54a of fluid channel 54; the end of the return cable fluid path 52 is in fluid communication with an output leg 54b of fluid channel 54. The input and output legs 54a and 54b of fluid channel 54 may be mounted on the same side (as shown in FIG. 4E) or on opposite sides of the internal heat conductor 36 (as shown in FIG. 6A). In the latter case, part of the U-shaped fluid channel is embedded in the backing material. Each pipe 50, 52 and 54 may be a plastic or metal tube filled with fluid having a high thermal conductivity.

The third preferred embodiment utilizes active movement, i.e., recirculating flow, of the cooling fluid in cooling pipes to cool the probe handle. This might be accomplished with a small micromotor 60 (see FIG. 6B) powered by the system. The micromotor 60 drives a pump 62 which pumps cooling fluid from a cooling fluid input line 64 to a cooling fluid output line 66 arranged inside the system connector 18. The cooling fluid input line 64 is in flow communication with the return cable fluid path 52 and the cooling fluid output line 66 is in flow communication with the input cable fluid path 50. Thus, pump 62, cooling fluid output line 66, input cable fluid path 50, fluid channel 54, return cable fluid path 52 and cooling fluid input line 64 form a closed circuit for recirculating flow of cooling fluid. As an alternative to the use of a motor to drive recirculation of the cooling fluid, recirculating flow may be driven by active cooling of a portion of the fluid circuit, thereby generating a thermal gradient which draws heat out of the probe handle. In either case, energy is expended in order to create cooling in the transducer handle.

Figure 4F:
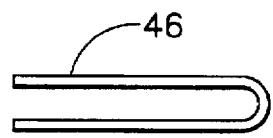

A variation on the active fluid coupling embodiment is to eliminate the internal heat conductor and simply embed the curved part of the U-shaped fluid channel 46 (see FIG. 4F) in the backing material.

In accordance with a fourth preferred embodiment shown in FIG. 7, a plurality of heat conductors 68 are implanted in the overall braid or shield 40 of the cable assembly. The overall shield 40 is in the shape of a braided annulus bounded by the cable jacket 34 on an outer periphery and by an internal sheath 70 on an inner periphery. The internal sheath 70 surrounds a bundle of coaxial cables 72. Each coaxial cable in turn comprises a jacket 74, braided shielding 76, dielectric 78 and a center conductor 80 arranged in well-known manner. The cable shield heat conductors 68 may be circumferentially distributed at equal angular intervals around the overall shield 40. The heat conductors may be made of any suitable material having a high coefficient of thermal conductivity, including gold threads woven into the overall braid (selected heat conductors with high coefficients of thermal conductivity) or a tube filled with fluid.

In the case of armored cable of the type shown in FIG. 8A, the bundle of coaxial cables is surrounded by a spiral armor 82. The armor cross section can be molded to provide one or more channels, which are filled with heat conductive material for transporting heat along the cable and away from the probe handle. Alternatively, as best seen in FIG. 8B, the armor can be molded to provide input and return channels 84a, 84b for recirculating fluid used to cool the transducer pallet.

Figure 9:
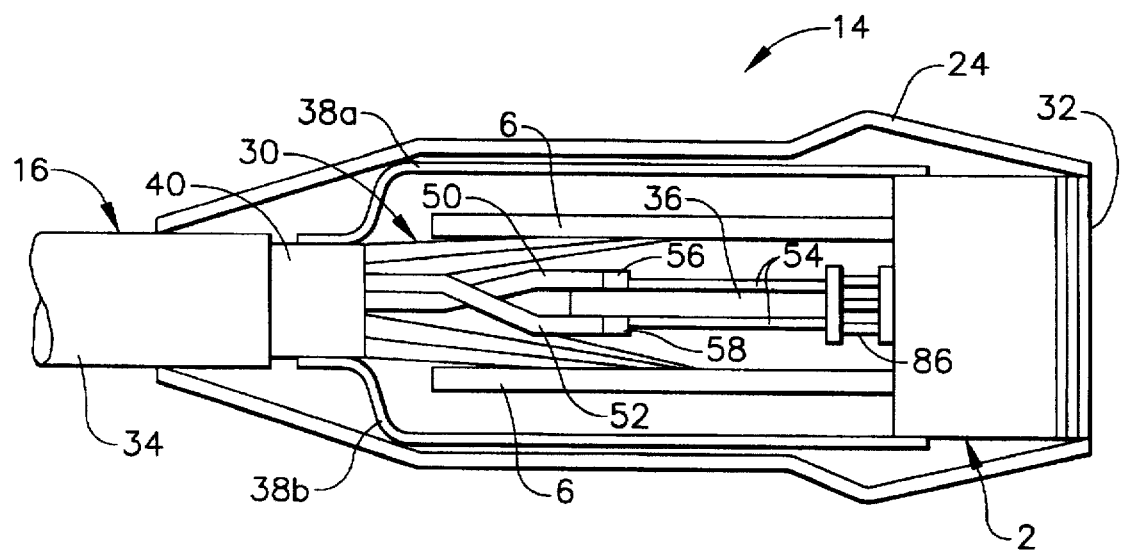
FIG. 9 is a schematic diagram showing the probe handle of an ultrasonic probe in accordance with a sixth preferred embodiment of the invention wherein the transducer pallet is thermally coupled to the cable via a semiconductor chiller.

Finally, in accordance with a sixth preferred embodiment shown in FIG. 9, a semiconductor chiller 86 is mounted in heat conductive relationship with the transducer pallet 2. Then an arrangement similar to that shown in FIGS. 6A and 6B is used to conductor the heat generated by the semiconductor chiller 86 to the outside environment. In this case, however, the internal heat conductor 36 is placed in heat conductive relationship with the semiconductor chiller 86, instead of being thermally coupled to the transducer pallet directly.

The foregoing preferred embodiments have been disclosed for the purpose of illustration. Variations and modifications which do not depart from the broad concept of the invention will be readily apparent to those skilled in the design of ultrasonic probes. All such variations and modifications are intended to be encompassed by the claims set forth hereinafter.

I claim:

1. An ultrasonic probe comprising a transducer array comprising a multiplicity of transducer elements, a layer of acoustic damping material acoustically coupled to a rear face of said transducer array, a first tube having a portion embedded in said acoustic damping material, a shielded cable comprising a multiplicity of electrical conductors and a second tube incorporated in said shielded cable, said second tube being in fluid communication with said first tube, and means for electrically connecting said transducer elements to said electrical conductors.

2. The ultrasonic probe as defined in claim 1, wherein said shielded cable further comprises a third tube, said first tube having an inlet in fluid communication with said second tube and an outlet in fluid communication with said third tube.

3. The ultrasonic probe as defined in claim 1, further comprising a pump and a motor, wherein said pump is in flow communication with said second and third tubes.

4. An ultrasonic probe comprising a probe handle and a shielded cable connected thereto, said shielded cable comprising a bundle of coaxial cables and an overall shield braid surrounding said bundle, said probe handle comprising a transducer pallet and a heat conductor which is thermally coupled to said transducer pallet and to said overall shield braid, and said transducer pallet comprising a multiplicity of transducer elements and a layer of acoustic damping material acoustically coupled to a rear face of said transducer array, wherein said heat conductor has a portion embedded in said acoustic damping material.

5. The ultrasonic probe as defined in claim 4, further comprising a mass of solder connecting said heat conductor to said overall shield braid.

6. An ultrasonic probe comprising a probe handle and a coaxial cable connected thereto, said coaxial cable comprising a jacket, braided shielding, dielectric and a center conductor, said probe handle comprising a transducer pallet and a heat conductor which is thermally coupled to said transducer pallet and said braided shielding, and said transducer pallet comprising a multiplicity of transducer elements and a layer of acoustic damping material acoustically coupled to a rear face of said transducer array, wherein said heat conductor has a portion embedded in said acoustic damping material.

7. An ultrasonic probe comprising a probe handle and a shielded cable connected thereto, said shielded cable comprising a bundle of coaxial cables, an overall shield braid surrounding said bundle and a first pipe segment filled with a first volume of a heat-conducting fluid thermally coupled to said overall shield braid, said probe handle comprising a transducer pallet, a solid member made of heat-conducting material which is thermally coupled to said transducer pallet and a second pipe segment filled with a second volume of said heat-conducting fluid thermally coupled to said solid member made of heat-conducting material, wherein said first and second pipe segments are connected to form a pipeline having no openings for fluid recirculation and having no barrier to the conduction of heat from said second volume to said first volume of said heat-conducting fluid, whereby heat from said transducer pallet is dissipated in said overall shield braid substantially without flow of said heat-conducting fluid.

8. The ultrasonic probe as defined in claim 7, wherein said solid member made of heat-conducting material is planar and said second pipe segment is fixed to said solid member.

9. An ultrasonic probe comprising a probe handle and a shielded cable connected thereto, said shielded cable comprising an electrical conductor and shielding braid, and said probe handle comprising a transducer pallet, a semiconductor chiller which is thermally coupled to said transducer pallet and a heat conductor which is thermally coupled to said semiconductor chiller and to said shielding braid.

10. An ultrasonic probe comprising a probe handle and a shielded cable connected thereto, said shielded cable comprising a bundle of coaxial cables and an overall shield braid surrounding said bundle, said probe handle comprising a transducer pallet, further comprising means for thermally coupling said transducer pallet to said overall shield braid, wherein said thermal coupling means comprise strands of heat-conducting material woven into said overall shield braid.

11. The ultrasonic probe as defined in claim 10, wherein said transducer pallet comprising a multiplicity of transducer elements and a layer of acoustic damping material acoustically coupled to a rear face of said transducer array, and said thermal coupling means comprise a heat conductor having a portion embedded in said acoustic damping material.

* * * * *